US010373328B2

(12) United States Patent
Maes et al.

(10) Patent No.: US 10,373,328 B2
(45) Date of Patent: *Aug. 6, 2019

(54) GENERATION OF A DIGITAL 3D MODEL OF AN OBJECT BASED ON PREDICTING A SHAPE OF THE OBJECT

(71) Applicant: MATERIALISE NV, Leuven (BE)

(72) Inventors: Jan Maes, Leuven (BE); Tom Cluckers, Hasselt (BE); Joris Van Deun, Leuven (BE)

(73) Assignee: Materialise N.V., Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,303

(22) Filed: Jul. 5, 2018

(65) Prior Publication Data

US 2018/0315206 A1 Nov. 1, 2018

Related U.S. Application Data

(63) Continuation of application No. 15/218,067, filed on Jul. 24, 2016, now Pat. No. 10,043,277, which is a (Continued)

(51) Int. Cl.
*G06K 9/00* (2006.01)
*G06T 7/55* (2017.01)
(Continued)

(52) U.S. Cl.
CPC .............. *G06T 7/55* (2017.01); *G06F 16/58* (2019.01); *G06F 16/5854* (2019.01); *G06F 19/00* (2013.01); *G06F 19/321* (2013.01); *G06K 9/6257* (2013.01); *G06K 9/66* (2013.01); *G06N 20/00* (2019.01); *G06T 7/0012* (2013.01);
(Continued)

(58) Field of Classification Search
None
See application file for complete search history.

(56) References Cited

U.S. PATENT DOCUMENTS 9,687,259 B2 6/2017 Pavlovskaia et al.
2002/0147392 A1 10/2002 Steines et al.
(Continued)

OTHER PUBLICATIONS

International Search Report dated May 7, 2015, in corresponding PCT Application No. PCT/EP20151050134.
(Continued)

*Primary Examiner* — Samah A Beg
(74) *Attorney, Agent, or Firm* — Patterson + Sheridan, LLP (57) ABSTRACT

Systems and methods for predicting shape are provided. A system for predicting shape can include a database, a training analysis module, a subject analysis module, and a prediction module. The database can store two sets of training models characterized by first and second parameters, respectively (e.g., bone and cartilage), as well as a subject model characterized by the first parameter (e.g., a bone model). The relationships between these models can be determined by a training analysis module and a subject module. Based on these relationships, the prediction module can generate a predicted shape characterized by the second parameter (e.g., a predicted cartilage model corresponding to the bone model).

19 Claims, 6 Drawing Sheets

Related U.S. Application Data continuation of application No. PCT/EP2015/050134, filed on Jan. 7, 2015.

(60) Provisional application No. 61/932,087, filed on Jan. 27, 2014.

(51) Int. Cl.

| | | |
|---|---|---|
| *G06N 20/00* | (2019.01) | |
| *G06F 16/58* | (2019.01) | |
| *G06F 16/583* | (2019.01) | |
| *G06T 17/20* | (2006.01) | |
| *G06T 19/20* | (2011.01) | |
| *G06F 19/00* | (2018.01) | |
| *G06K 9/62* | (2006.01) | |
| *G06K 9/66* | (2006.01) | |
| *G06T 7/00* | (2017.01) | |
| *H04N 21/61* | (2011.01) | |
| *G06T 7/50* | (2017.01) | |
| *G06T 7/586* | (2017.01) | |
| *G16H 30/40* | (2018.01) | |
| *G16H 50/50* | (2018.01) | |

(52) U.S. Cl.
CPC ............... *G06T 7/50* (2017.01); *G06T 7/586* (2017.01); *G06T 17/20* (2013.01); *G06T 19/20* (2013.01); *G16H 30/40* (2018.01); *G16H 50/50* (2018.01); *H04N 21/61* (2013.01); G06T 2207/10088 (2013.01); G06T 2207/10116 (2013.01); G06T 2207/30008 (2013.01); G06T 2210/41 (2013.01)

(56) References Cited

U.S. PATENT DOCUMENTS

| | | |
|---|---|---|
| 2007/0015995 A1 | 1/2007 | Lang et al. |
| 2007/0122018 A1 | 5/2007 | Zhou et al. |
| 2007/0203430 A1 | 8/2007 | Lang et al. |
| 2008/0200840 A1 | 8/2008 | Tamez-Pena et al. |
| 2010/0153076 A1 | 6/2010 | Bellettre et al. |
| 2011/0270072 A9 | 11/2011 | Feilkas et al. |
| 2011/0304332 A1 | 12/2011 | Mahfouz |
| 2012/0265496 A1 | 10/2012 | Mahfouz |
| 2013/0294667 A1* | 11/2013 | Zheng ............... G06T 7/0012 382/131 |
| 2014/0086465 A1* | 3/2014 | Wu ............... G06T 7/0012 382/131 |
| 2014/0161334 A1 | 6/2014 | Wang et al. |
| 2014/0169522 A1 | 6/2014 | Hoshino |
| 2014/0294276 A1* | 10/2014 | Song ............... G06T 7/75 382/132 |
| 2015/0150529 A1 | 6/2015 | Hoshino et al. |
| 2015/0223777 A1* | 8/2015 | Rasoulian ........... A61B 8/0875 600/461 |
| 2016/0015465 A1 | 1/2016 | Steines et al. |
| 2016/0022370 A1 | 1/2016 | Pavlovskaia et al. |
| 2016/0267352 A1 | 9/2016 | Van Deun |
| 2017/0091574 A1* | 3/2017 | Udupa ............... G06T 7/11 |
| 2017/0258526 A1 | 9/2017 | Lang |
| 2018/0360544 A1* | 12/2018 | Vanheule ........... A61B 34/10 |

OTHER PUBLICATIONS

Johnson, J.M. (2013). "Analysis, Segmentation and Prediction of Knee Cartilage Using Statistical Shape Models." PhD diss., University of Tennessee, 2013. http//trace.tennessee.edu/utk_graddiss/2583.

Lindner et al., (2013). Development of a fully automatic shape model matching (FASMM) system to derive statistical shape models from radiographs: application to the accurate capture and global representation of proximal femur shape. Osteoarthiritis and cartilage, 21(10), 1537-1544.

* cited by examiner

GENERATION OF A DIGITAL 3D MODEL OF AN OBJECT BASED ON PREDICTING A SHAPE OF THE OBJECT

CROSS-REFERENCES

The present application is a continuation of U.S. patent application Ser. No. 15/218,067, filed Jul. 24, 2016, which is a continuation application of International Application No. PCT/EP2015/050134, filed Jan. 7, 2015 (and published by the International Bureau on Jul. 30, 2015 as International Publication No. WO 2015/110282), which claims the benefit of U.S. Provisional Application No. 61/932,087, filed Jan. 27, 2014. The entire content of each of the above-referenced patent applications is hereby incorporated by reference.

BACKGROUND OF THE INVENTION

Field of the Invention

This application relates to prediction of shapes from shape models. More particularly, this application relates to predicting a patient- or case-specific shape from a statistical shape model.

Description of the Related Technology

Statistical models of shape have been used for some time to provide automated interpretation of images. The basic idea used by the models is to establish, from a training set, a pattern of "legal" variation in the shapes and spatial relationships of structures in a given class of images (the class of images may be for example face images, hand images, etc.). Statistical analysis is used to give an efficient parameterization of the pattern of legal variation, providing a compact representation of shape. The statistical analysis also provides shape constraints which are used to determine whether the shape of a structure in an analyzed image is a plausible example of the object class of interest.

A statistical shape model can be constructed by segmenting images of training shapes, which are commonly 2D or 3D shapes. Statistical shape models can be used in the medical field, in which case the images used to develop the model can be, for example, x-rays, CT scans, or MRIs. Statistical shape models can be used for a variety of medical purposes, for example to analyze the shape of a patient's anatomy, or to create a model of a patient's anatomical structure, for example to design patient-specific surgical guides.

SUMMARY

In accordance with embodiments of the present invention, there are provided a system, a method, and a computer-readable medium carrying instructions for predicting a shape according to the appended claims.

More specifically, in a first aspect of the invention there is provided a system for predicting a shape. The system comprises at least one database configured to store a first set of training models, a second set of training models, and a subject model, wherein each model in the first set of training models corresponds to an model in the second set of training models, wherein the first set of training models and the subject model are characterized by a first parameter, and wherein the second set of training models is characterized by a second parameter. The system also comprises a training analysis module configured to determine a relationship between the first set of training models and the second set of training models. The system further comprises a subject analysis module configured to determine a relationship between the subject model and the first set of training models, and a prediction module configured to generate a predicted shape based on the relationship between the first set of training models and the second set of training models and on the relationship between the subject model and the first set of training models. In an embodiment of the first aspect, the training analysis module is configured to determine an average shape for the first set of training models, determine a decomposition of the first set of training models, determine an average shape for the second set of training models, and determine a decomposition of the second set of training models. In another embodiment of the first aspect, the subject analysis module is configured to determine a fitting vector. In another embodiment of the first aspect, the prediction module is configured to generate a predicted shape by modifying a subject model. In another embodiment of the first aspect, the prediction module is configured to generate a predicted shape based at least in part on a fitting vector.

In a second aspect, there is provided a computer implemented method of predicting a shape. The method comprises determining a relationship between a first set of training models and a second set of training models, each model in the first set of training models corresponding to an model in the second set of training models, the first set of training models being characterized by a first parameter; the second set of training models being characterized by a second parameter. The method also comprises determining a relationship between a subject model and the first set of training models, the subject model being characterized by the first parameter. The method further comprises generating a predicted shape based on the relationship between the first set of training models and the second set of training models and on the relationship between the subject model and the first set of training models, the predicted shape being characterized by the second parameter. In another embodiment of the second aspect, the first set of training models comprises anatomical models and the first parameter is bone. In another embodiment of the second aspect, the second set of training models comprises anatomical models and the second parameter is cartilage. In another embodiment of the second aspect, the first set of training models and the second set of training models are derived from MRI images, and wherein the subject model is derived from an x-ray image. In another embodiment of the second aspect, determining a relationship between the first set of training models and the second set of training models comprises determining an average shape for the first set of training models, determining a decomposition of the first set of training models, determining an average shape for the second set of training models, and determining a decomposition of the second set of training models. In another embodiment of the second aspect, determining a relationship between the subject model and the first set of training models comprises determining a fitting vector. In another embodiment of the second aspect, generating a predicted shape comprises modifying the subject model. In another embodiment of the second aspect, generating a predicted shape is based at least in part on the fitting vector. In a further embodiment of the second aspect, the method can further comprise identifying at least one region of the predicted shape having an accuracy above a threshold accuracy level.

In a third aspect, there is provided a non-transitory computer readable medium comprising computer executable instructions stored thereon which when executed by a processor cause a computer to perform a method of predicting a shape. The method can comprise determining a relationship between a first set of training models and a second set of training models, each model in the first set of training models corresponding to an model in the second set of training models, the first set of training models being characterized by a first parameter; the second set of training models being characterized by a second parameter. The method can further comprise determining a relationship between a subject model and the first set of training models, the subject model being characterized by the first parameter. The method can also comprise generating a predicted shape based on the relationship between the first set of training models and the second set of training models and on the relationship between the subject model and the first set of training models, the predicted shape being characterized by the second parameter.

DETAILED DESCRIPTION OF CERTAIN INVENTIVE EMBODIMENTS

Embodiments of this application relate to systems and methods for predicting a shape from a subject model. In various embodiments, a shape can be predicted by determining a relationship between two sets of training models, determining a relationship between the subject model and the first set of training models, and generating a predicted shape based on these relationships. The first set of training models and the subject model can be characterized by a first parameter, while the second set of training models and the predicted shape can be characterized by a second and corresponding (or potentially corresponding) parameter. For purposes of illustration, in a medical application, the first and second parameters can be bone and cartilage, respectively, the subject model can be a model of a particular joint's bone contour, and embodiments can facilitate the prediction of that same joint's cartilage contour. Thus, in the medical field, embodiments can be used to predict the shape of a particular patient's cartilage contour (which would otherwise only be visible in an MRI image) from an x-ray image showing only that patient's bone contour. Shape prediction in such a context can allow for the development of patient-specific anatomical models or surgical guides while avoiding the expense of an MRI. In another medical application, first and second sets of training models can comprise heart models in first and second phases, respectively, of a heartbeat. Shape prediction in such a context can allow for the prediction of heartbeat patterns using a subject image showing only one phase of a patient's heart.

Figure 1:
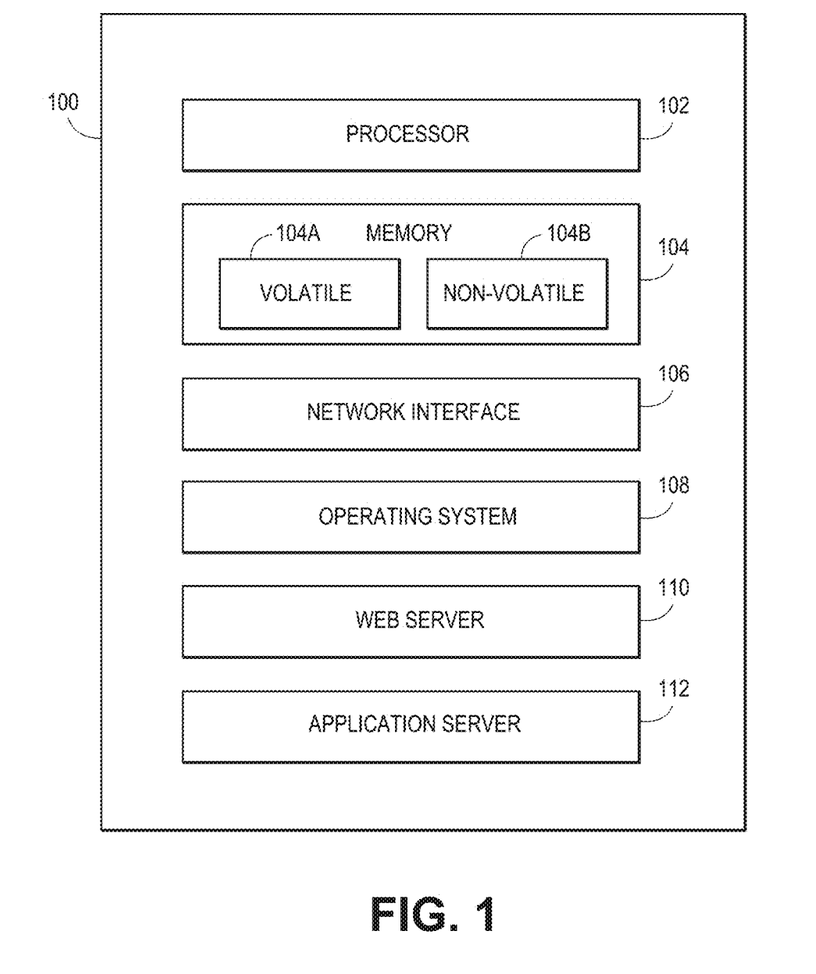
FIG. 1 is a block diagram of one example of a computing environment suitable for practicing various embodiments disclosed herein.

The systems and methods described herein may be implemented using one or more computer systems. Turning now to FIG. 1, an example is provided of a computer system 100 suitable for practicing various embodiments. The computer system 100 may generally take the form of computer hardware configured to execute certain processes and instructions in accordance with one or more embodiments described herein. The computer hardware may be a single computer or it may be multiple computers configured to work together. The computer system 100 includes a processor 102. The processor is generally configured to execute computer instructions to carry out certain tasks related to shape prediction. The processor 102 may be a standard personal computer processor such as those designed and/or distributed by Intel, Advanced Micro Devices, Apple, ARM, or Motorola. The processor 102 may also be a more specialized processor tailored for image processing and analysis. The system 100 may also include memory 104. The memory 104 may include volatile memory 104A such as some form of random access memory. The volatile memory 104A may be configured to load executable software modules into memory so that the software modules may be executed by the processor 102 in a manner well known in the art. The software modules may be stored in a non-volatile memory 104B. The non-volatile memory 104B may take the form of a hard disk drive, a flash memory, a solid state hard drive or some other form of non-volatile memory. The non-volatile memory 104B may also be used to store non-executable data, such database files and the like.

Figure 2:
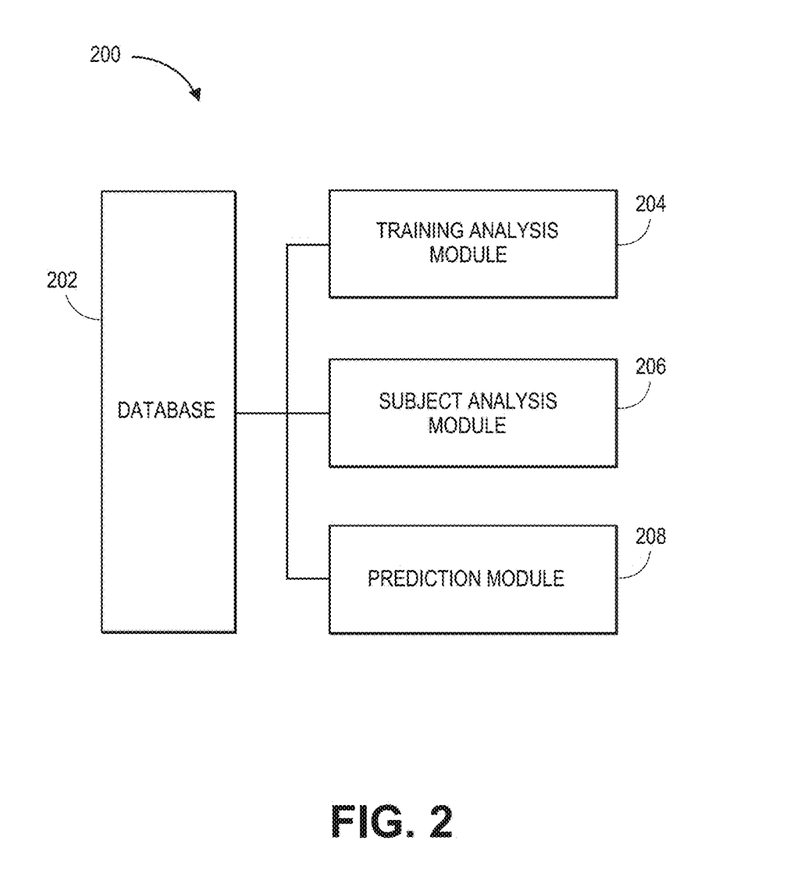
FIG. 2 is a high level system diagram of a computing system that may be used in accordance with one or more embodiments.

The computer system 100 also may include a network interface 106. The network interface may take the form of a network interface card and its corresponding software drivers and/or firmware configured to provide the system 100 with access to a network (such as the Internet, for example). The network interface card 106 may be configured to access various different types of networks. For example the network interface card 106 may be configured to access private networks that are not publicly accessible. The network interface card 106 may also be configured to access wireless networks such using wireless data transfer technologies such as EVDO, WiMax, or LTE network. Although a single network interface card 106 is shown in FIG. 2, multiple network interface cards 106 may be present in order to access different types of networks. In addition, the network interface card 106 may be configured to allow access to multiple different types of networks.

An operating system 108 is also included in the computer system 100. The operating system 108 may be a well-known general operating system such as Linux, Windows, ChromeOS, or MacOS which is designed to provide a platform from which computer software applications may be executed by the processor 102. Alternatively, the operating system 108 may also be a special purpose operating system designed specifically for image processing and analysis applications. Still further, the operating system 108 may be a mobile operating system such as Android, Windows Mobile, or IOS.

Running on the operating system 108 may be web server software 110. The web server software 110 may be a standard off the shelf web server product such as Apache, Internet Information Server, or some other web server software. Alternatively, the web server may form a part of the operating system 108, or it may be a specialized HTTP server which is configured specifically to deliver image- or analysis-related web pages to browsing software via a network such as the Internet, or some other local area network or wide area network. The web server software 110 may be stored in the memory 104 for access by the processor 102 to execute on the operating platform provided by the operating system 108.

The computer system 100 may further include an application server 112. The application server 112 may include computer hardware and/or software which is configured to provide network-based applications which may run natively on the computer system 100, or be accessed via the web server 110, or both. The application server may be configured to allow for the distribution, use, and maintenance of a system for predicting a shape that will be discussed in detail below.

With reference now to FIG. 2, a computer-based system 200 for predicting a shape according to an embodiment is illustrated. The system 200 may be comprised of one or more computers such as computer 100 shown in FIG. 1 and discussed above. The system 200 can include a database 202 which may be configured to perform various functions within the system 200, such as, for example, capturing, storing, and/or providing access for software applications and other devices to image and/or model data stored in the database. The database 202 may be a relational database, an object oriented database, an object relational database, or any other type of database suitable for performing its intended function. The database 202 can be configured to store raw 2D and/or 3D image data, such as, for example, medical image data from photographs, CT scans, MRIs, x-rays, and the like. Alternatively or in addition, the database 202 can be configured to store 2D and/or 3D models, such as, for example, training models and/or patient-specific models of bone shapes, cartilage shapes, and/or soft tissue shapes. The database 202 may include source- or shape-specific data (either anonymous or protected) which is related to image or model data stored in the database. The database 202 may also include shape-specific data about the images or models, such as, for example, information about landmark points and/or curves associated with the images or models. The shape-specific data can be manually indicated, for example by conversion engineers, or may be automatically indicated, for example by a computer-aided design ("CAD") or preprocessing tool, or simply by the location of a cut or section on the original shape (e.g., the intersection of a bone and a plane on which it is cut). In some embodiments, the image or model data can include one or more sets of training images or training models, as well as one or more subject images or models (e.g., a patient-specific model) for use in the prediction of a shape. A set of training shapes can include any number of images or models. For example, a training set can include about 10, 50, 100, 500, or 1000 shapes, or a number of shapes less than, greater than, or within a range defined by any of these numbers.

As illustrated in FIG. 2, the system 200 may further include a training analysis module 204 which is configured to analyze the 2D and/or 3D training images or models in the database 202, optionally in addition to any associated shape-specific data, and perform various functions in connection therewith. For example, the training analysis module 204 can be configured to perform CAD, preprocessing, parameterization, meshing (e.g. triangulation) and/or other modeling functions. The training analysis module 204 can also be configured to perform various analysis functions, including, for example, principal component analysis functions. The training analysis module 204 may take the form of a computing device having 2D and/or 3D image processing and/or modeling software installed in its operating system. The training analysis module 202 may be comprised primarily or entirely of software, or it may be comprised of a combination of hardware and software, or in still other embodiments, specialized hardware such as ASIC or other types of microprocessors. In some embodiments, certain modeling and/or analysis functionality may be provided by one software application, while other modeling and/or analysis functionality can be provided by one or more separate computer applications. Alternatively, all of these functionalities may be provided in a single computer program.

As also illustrated in FIG. 2, the system 200 may further include a subject analysis module 206 which is configured to analyze the 2D and/or 3D subject image(s) or model(s) in the database 202, optionally in addition to any associated shape-specific data, and perform various functions in connection therewith. For example, the subject analysis module 206 can be configured to perform CAD, preprocessing, parameterization, meshing (e.g. triangulation) and/or other modeling functions. The subject analysis module 206 can also be configured to perform various analysis functions, including, for example, principal component analysis functions. The subject analysis module 206 may take the form of a computing device having 2D and/or 3D image processing and/or modeling software installed in its operating system. The subject analysis module 206 may be comprised primarily or entirely of software, or it may be comprised of a combination of hardware and software. In some embodiments, certain modeling and/or analysis functionality may be provided by one software application, while other modeling and/or analysis functionality can be provided by one or more separate computer applications. Alternatively, all of these functionalities may be provided in a single computer program. Further, although illustrated in FIG. 2 as separate modules, in some embodiments, the training analysis module 204 and the subject analysis module 206 can be provided together in a single computer program.

As further illustrated in FIG. 2, the system 200 may further include a prediction module 208. The prediction module 208 can be configured to predict a shape on the basis of information about the subject image or model (which information can be received from the subject analysis module 206), information about the training images or models (which information can be received from the training analysis module 204), and information about the relationship between the subject model and the training models (which information can be received from the training analysis module 204 and/or the subject analysis module 206). For example, the subject analysis module 206 can be configured to perform CAD, preprocessing, parameterization, meshing (e.g. triangulation) and/or other modeling functions. The prediction module 208 may take the form of a computing device having 2D and/or 3D image processing and/or modeling software installed in its operating system. The prediction module 208 may be comprised primarily or entirely of software, or it may be comprised of a combination of hardware and software. In some embodiments, certain modeling and/or analysis functionality may be provided by one software application, while other modeling and/or analysis functionality can be provided by one or more separate computer applications. Alternatively, all of these functionalities may be provided in a single computer program. Further, although illustrated in FIG. 2 as separate modules, in some embodiments, the training analysis module 204, the subject analysis module 206, and the prediction module 208 can be provided together in a single computer program.

In some embodiments, the training analysis module 204, the subject analysis module 206, and/or the prediction module 208 may include a numerical computing system such as the MATLAB® environment available from Math-Works of Natick, Mass. Other numerical analysis software packages may be utilized, including but not limited to C++, Python, Maple, FreeMat, IGOR Pro, jBEAM, and the like.

It is to be appreciated that the system 200 described in FIG. 2 is merely one of many suitable environments in which the systems and methods disclosed herein may be practiced. A skilled artisan will readily appreciate that the system 200 may be connected to a computer network, or it may be standalone and isolated from any computer networks. Moreover, a skilled artisan will also appreciate that although the various components described in FIG. 2 are described separately, they may be functionally combined into fewer modules, or alternatively divided into additional modules.

Figure 3:
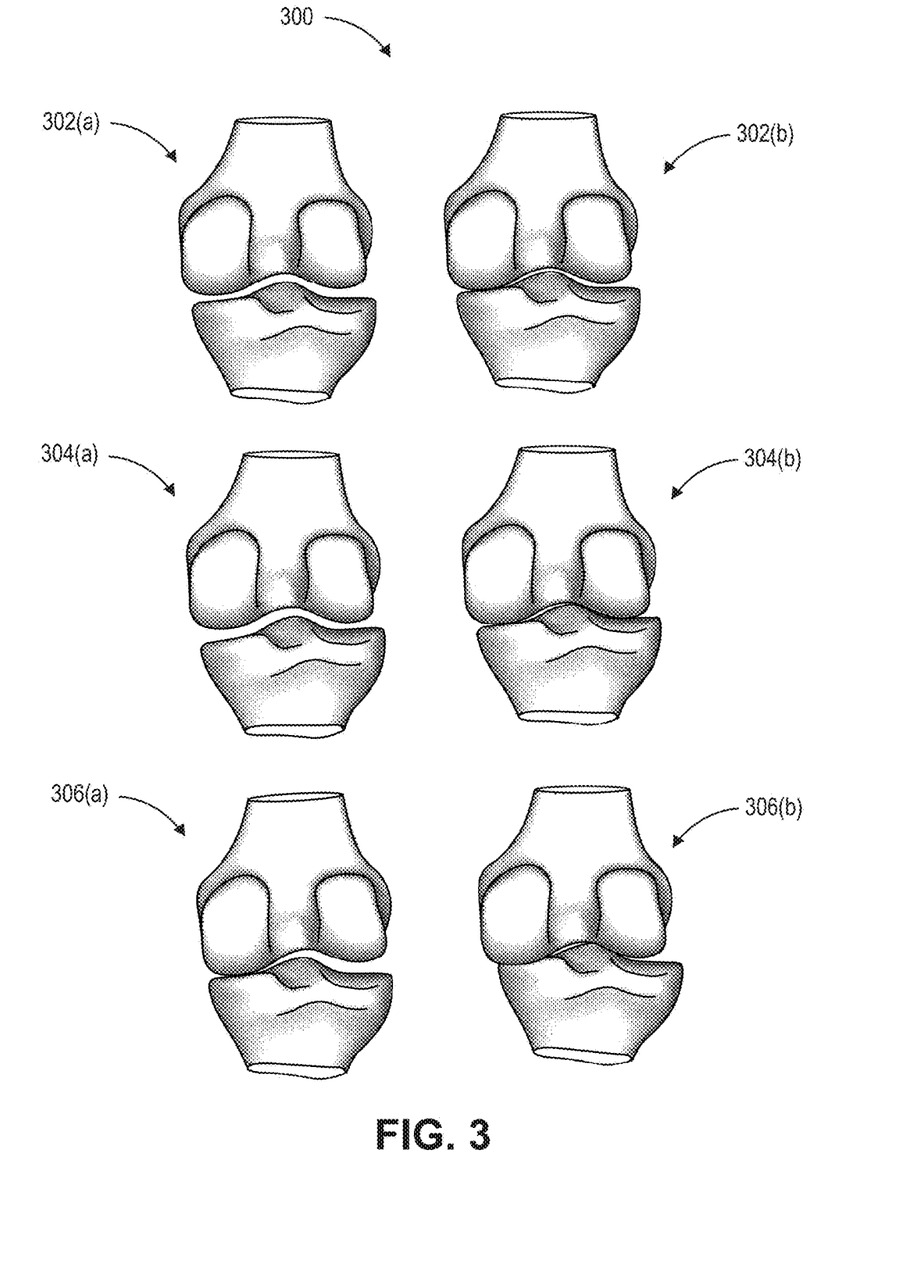
FIG. 3 illustrates examples of first and second sets of training images which can be used in one or more embodiments.

FIG. 3 illustrates examples of first and second sets of training images which can be used in one or more embodiments. The first set of training images 302(*a*), 304(*a*), 306(*a*) are bone models that represent the shape of the femurs and tibias of three different patients near the knee joint as characterized by bone only, without cartilage. The second set of training images 302(*b*), 304(*b*), 306(*b*) are cartilage models that represent the shape of the femurs and tibias of the same three patients, respectively, as characterized by cartilage. As can be seen in FIG. 3, the cartilage models tend to be slightly larger than the corresponding bone models at the knee joint near the gap between the femur and tibia. The images 302(*a*), 302(*b*), 304(*a*), 304(*b*), 306(*a*), 306(*b*) can be constructed from, for example, medical scans (e.g., MRIs) of patients, for example using commercially available CAD (Computer Aided Design) and/or other imaging software.

In embodiments, the first and second sets of training images can be segmented to produce models of each training image. This can involve, for example, segmenting the images in each set to produce models of each image; finding correspondences between pairs of models from the first set and the second set; and defining each model (e.g., using Cartesian, polar, or spherical coordinates) in a vector. The vectors for the training models can then be combined in a matrix. A subject image or images can be also defined in one or more vectors.

Figure 4A:
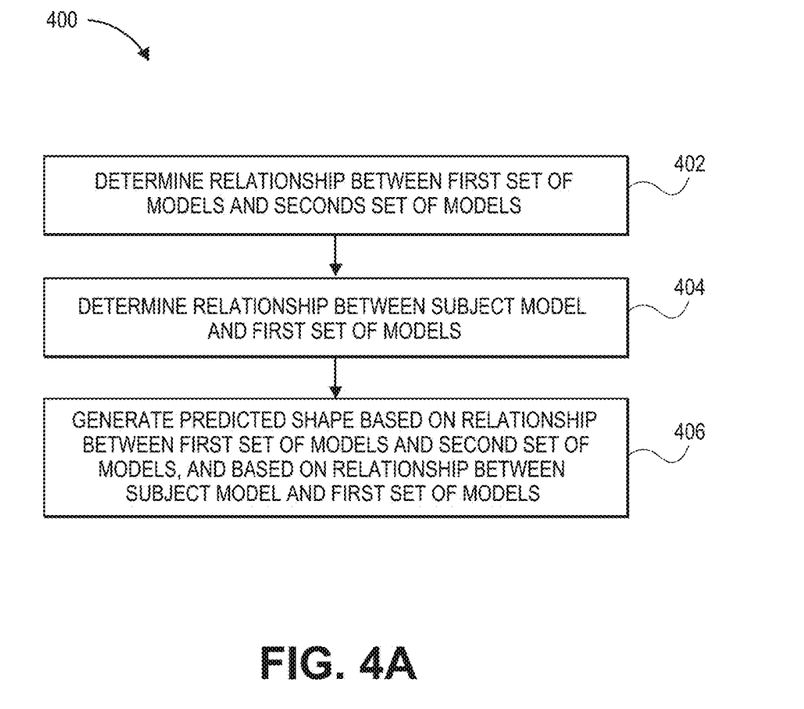
FIG. 4A is a flowchart illustrating a method of predicting a shape according to one or more embodiments.

With reference now to FIG. 4A, a process 400 for predicting a shape according to one or more embodiments is illustrated. The process 400 begins at block 402, which includes determining a relationship between a first set of models and a second set of models. The process 400 can move to block 404, which includes determining a relationship between a subject model and the first set of models. In some embodiments, the process implemented at block 404 (i.e., determining a relationship between a subject model and the first set of models) can include determining a fitting vector, for example using a fitting algorithm. The fitting vector can be, for example, a suitable coefficient vector to define the subject model in terms of the first training set. The process 400 can then move to block 406, which includes generating a predicted shape based on the relationship between the first set of models and the second set of models, and based on the relationship between the subject model and the first set of models.

Figure 4B:
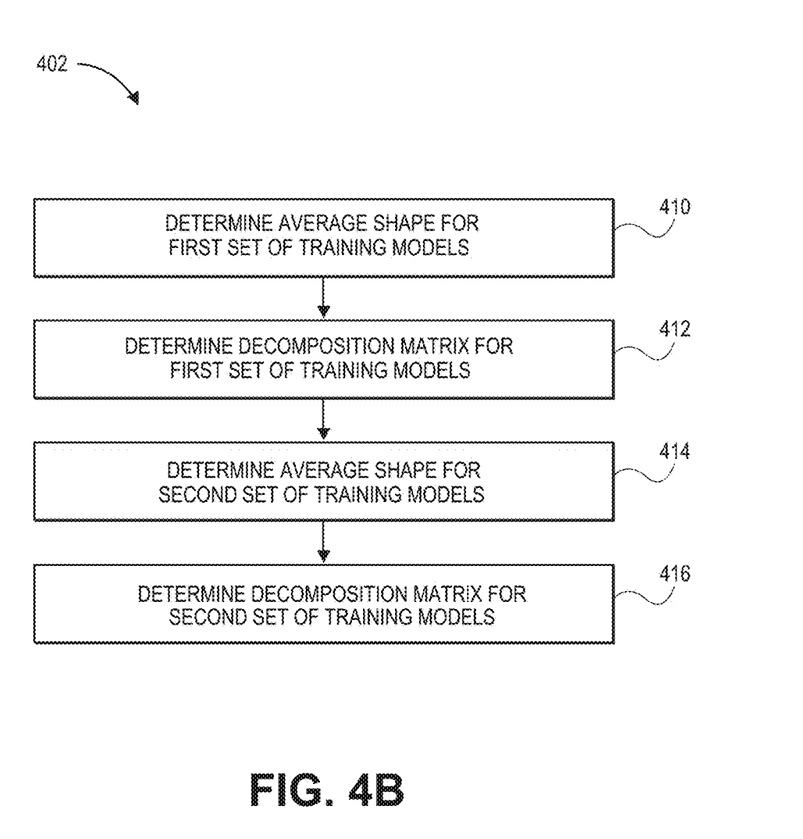
FIG. 4B is a flowchart illustrating sub-steps in a method of predicting a shape according to one or more embodiments.

In embodiments, one or more steps and/or substeps in the process 400 can be implemented using principal component analysis. For example, as further illustrated in FIG. 4B, the process implemented at block 402 (i.e., determining a relationship between a first set of models and a second set of models) can include, at block 410, determining an average segmentation or shape for the first set of training models. At block 412, the process 402 can include determining a decomposition matrix for the first set of training models. At block 414, the process 402 can include determining an average segmentation or shape for the second set of training models. At block 416, the process 402 can include determining a decomposition matrix for the second set of training models. In some embodiments, block 406 (i.e., generating a predicted shape) can be performed using the results of principal component analysis (e.g., the results of blocks 410, 412, 414, and 416. In embodiments, the mentioned relationships (e.g., the relationship between the first set of models and the second set of models) can be determined once, and then used repeatedly with different subject models to generate a predicted shape for each subject model.

The following are examples of equations that can be utilized to generate a predicted shape in some embodiments:

$$S_S = A * c \qquad \text{Equation 1}$$

$$S_S = \mu + U_1 * e \qquad \text{Equation 2}$$

$$S_P = B * d \qquad \text{Equation 3}$$

$$S_P = \eta + U_2 * e \qquad \text{Equation 4}$$

Where:

$S_S$ is a vector defining the subject model;

A is a matrix defining the first set of training models;

c is a fitting vector (e.g., a coefficients vector) representing a relationship between the subject model and the first set of training models;

μ is a weighted average segmentation of the first set of training models (e.g., the sum of all vectors for the first set, divided by the number of such vectors, gives an equally weighted average segmentation);

$U_1$ is a decomposition matrix for the first set of training models;

e is an alternative fitting vector (e.g. a coefficients vector) representing a relationship between the subject model and the first set of training models;

$S_P$ is a vector defining the predicted model or shape;

B is a matrix defining the second set of training models;

d is a fitting vector (e.g., a coefficients vector) representing a relationship between the predicted shape model and the second set of training models;

η is a weighted average segmentation of the second set of training models (e.g., the sum of all vectors for the second set, divided by the number of such vectors, gives an equally weighted average segmentation); and $U_2$ is a decomposition matrix for the second set of training models.

In one embodiment, a fitting algorithm can be used to obtain a fitting vector e, based on information about a subject model $S_M$ and information about a first set of training models (see, e.g., Equation 2). A relationship $U_2$ can then be determined which allows a predicted shape $S_P$ to be defined in terms of an average shape η for the second set of training models, using a relationship e between the subject model and the first set of training models (see, e.g., Equation 4).

In one embodiment, c can be determined as follows:

$$A*c = \mu + U_1*e \quad \text{Equation 5}$$

$$c = A^{-1}*(\mu + U_1*e) \quad \text{Equation 6}$$

Where $A^{-1}$ is the pseudo-inverse of the matrix A. A predicted shape $S_P$ can then be determined using the following equation, in which vector d in Equation 3 is simply replaced by vector c from Equation 6:

$$S_P = B*c = B*A^{-1}*(\mu + U_1*e) = B*A^{-1}*\mu + B*U_1*e \quad \text{Equation 7}$$

Then, $\eta$ and $U_2$ can be defined as follows:

$$\eta = B*A^{-1}*\mu \quad \text{Equation 8}$$

$$U_2 = B*U_1 \quad \text{Equation 9}$$

And the predicted shape $S_P$ becomes:

$$S_P = \eta + U_2*e \quad \text{Equation 10}$$

In such an embodiment, instead of the arithmetic mean of the second set of training models, $\eta$ can be a weighted average of the second set of training models, where the weights are determined by the factor $A^{-1}*\mu$.

In another embodiment, $\eta$ can be the real arithmetic mean of the second set of training models. In such an embodiment, a singular value decomposition of matrix $[A-\mu]$ can be used, where $[A-\mu]$ is defined as matrix A where we have subtracted vector $\mu$ from each column of matrix A; e.g.:

$$[A-\mu] = U_1*\Sigma_1*V_1^T \quad \text{Equation 11}$$

This is consistent with Equation 1 and Equation 2 which provide one way of computing a decomposition $U_1$ for a set of training models. Equation 2 can be rewritten as:

$$S_S = \mu + [A-\mu]*f \quad \text{Equation 12}$$

where f satisfies:

$$f = V_1*\Sigma_1^{-1}*e \quad \text{Equation 13}$$

Equation 2 can also be rewritten as any of the following relationships:

$$S_S = \mu + [A\mu]*f \quad \text{Equation 14}$$

$$S_S = \mu + (U_1*\Sigma_1*V_1^T)*f \quad \text{Equation 15}$$

$$S_S = \mu + (U_1*\Sigma_1*V_1^T)*(V_1*\Sigma_1^{-1}*e) \quad \text{Equation 16}$$

Vector f can be used to predict $S_P$ as follows:

$$S_P = \eta + [B-\eta]*f \quad \text{Equation 17}$$

Thus, if $U_2$ is defined as follows:

$$U_2 = [B-\eta]*V_1*\Sigma_1^{-1} \quad \text{Equation 18}$$

then Equation 4 can be rewritten as any of the following relationships:

$$S_P = \eta + [B-\eta]*f \quad \text{Equation 19}$$

$$S_P = \eta + [B-\eta]*V_1*\Sigma_1^{-1}*e \quad \text{Equation 20}$$

Figure 5A:
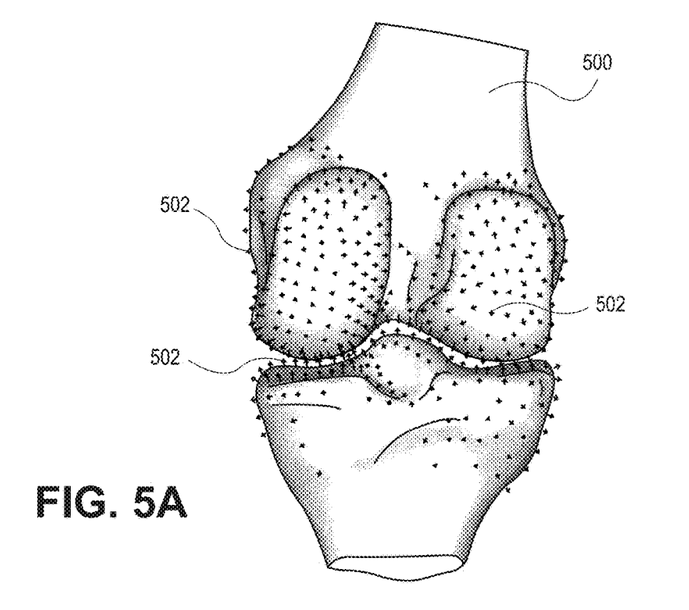
FIG. 5A shows an example of a bone model with a corresponding predicted cartilage shape shown as vectors projecting from the surface of the bone model, in accordance with one embodiment.
Figure 5B:
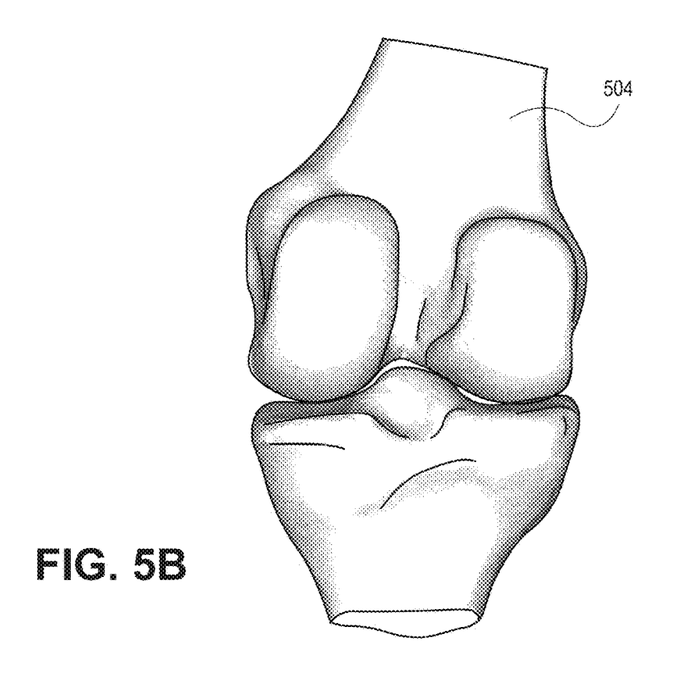
FIG. 5B shows the predicted cartilage shape indicated by vectors in FIG. 5A.

FIG. 5A shows an example of a subject model comprising a bone model, with a corresponding predicted cartilage shape shown as vectors projecting from the surface of the bone model, in accordance with one embodiment. The bone model can be generated from an x-ray image, with markers used when taking the x-ray to facilitate 3D positioning of the knee and the x-ray image during image processing. In some embodiments, contours can be indicated on the x-rays (e.g., manually) and fit to a statistical shape model in order to generate the bone model. FIG. 5B shows the predicted cartilage shape indicated by the vectors in FIG. 5A.

In some embodiments, a predicted shape can be used to perform surgical planning (e.g., to plan areas for drilling or debridement). One or more patient-specific surgical guides (e.g., a structure than can be placed on the patient's anatomy during surgery and used to guide surgical procedure) can also be designed using the predicted cartilage shape. In some embodiments, accuracy maps can be generated which indicate, on the predicted shape, regions of higher and lower accuracy (e.g., which regions which are typically highly reliable, and which regions should be avoided for guide design or otherwise not relied upon).

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A system for generating a digital 3D model of an object of an object type based on predicting a shape of the object, the system comprising:
    a memory configured to store at least one database configured to store a first set of training models corresponding to 2D models of the object type, a second set of training models corresponding to 3D models of the object type, and a subject model corresponding to a 2D model corresponding to the object, wherein each 2D model in the first set of training models corresponds to a 3D model in the second set of training models;
    a processor configured to:
        determine an average shape for the first set of training models;
        determine a decomposition of the first set of training models;
        determine an average shape for the second set of training models;
        determine a decomposition of the second set of training models;
        determine a relationship between the first set of training models and the second set of training models as function of the average shape for the first set of training models, the decomposition of the first set of training models, the average shape for the second set of training models, and the decomposition of the second set of training models;
        determine a relationship between the subject model and the first set of training models; and
        generate the digital 3D model of the object based on a predicted shape of the object based on the relationship between the first set of training models and the second set of training models and on the relationship between the subject model and the first set of training models.

2. The system of claim 1, wherein to determine the relationship between the subject model and the first set of training models comprises to determine a fitting vector.

3. The system of claim 2, wherein to generate the digital 3D model of the object based on the predicted shape comprises to generate the predicted shape based at least in part on the fitting vector.

4. The system claim 1, wherein to generate the digital 3D model of the object based on the predicted shape comprises to generate the predicted shape by modifying the subject model.

5. The system of claim 1, wherein the object type comprises anatomy of a patient.

6. A computer implemented method of generating a digital 3D model of an object of an object type based on predicting a shape of the object, the method comprising:
   determining an average shape for a first set of training models comprising 2D models of the object type;
   determining a decomposition of the first set of training models;
   determining an average shape for a second set of training models comprising 3D models of the object type;
   determining a decomposition of the second set of training models;
   determining a relationship between the first set of training models and the second set of training models as a function of the average shape for the first set of training models, the decomposition of the first set of training models, the average shape for the second set of training models, and the decomposition of the second set of training models, each model in the first set of training models corresponding to a model in the second set of training models;
   determining a relationship between a subject model corresponding to a 2D model corresponding to the object and the first set of training models; and
   generating the digital 3D model of the object based on a predicted shape of the object based on the relationship between the first set of training models and the second set of training models and on the relationship between the subject model and the first set of training models.

7. The computer implemented method of claim 6, wherein the first set of training models are derived from x-ray images, and wherein the subject model is derived from an x-ray image.

8. The computer implemented method of claim 7, wherein the second set of training models are derived from one of CT scans and MRI scans.

9. The computer implemented method of claim 6, wherein the second set of training models are derived from one of CT scans and MRI scans.

10. The computer implemented method of claim 6, wherein determining the relationship between the subject model and the first set of training models comprises determining a fitting vector.

11. The computer implemented method of claim 10, wherein generating the digital 3D model of the object based on the predicted shape is based at least in part on the fitting vector.

12. The computer implemented method of claim 6, wherein generating the digital 3D model of the object based on the predicted shape comprises modifying the subject model.

13. A non-transitory computer readable medium comprising computer executable instructions stored thereon which when executed by a processor cause a computer to perform a method of generating a digital 3D model of an object of an object type based on predicting a shape of the object, the method comprising:
   determining an average shape for a first set of training models comprising 2D models of the object type;
   determining a decomposition of the first set of training models;
   determining an average shape for a second set of training models comprising 3D models of the object type;
   determining a decomposition of the second set of training models;
   determining a relationship between the first set of training models and the second set of training models as a function of the average shape for the first set of training models, the decomposition of the first set of training models, the average shape for the second set of training models, and the decomposition of the second set of training models, each model in the first set of training models corresponding to a model in the second set of training models;
   determining a relationship between a subject model and the first set of training models, the subject model being a 2D model corresponding to the object; and
   generating the digital 3D model of the object based on a predicted shape of the object based on the relationship between the first set of training models and the second set of training models and on the relationship between the subject model and the first set of training models.

14. The non-transitory computer readable medium of claim 13, wherein the first set of training models are derived from x-ray images, and wherein the subject model is derived from an x-ray image.

15. The non-transitory computer readable medium of claim 14, wherein the second set of training models are derived from one of CT scans and MRI scans.

16. The non-transitory computer readable medium of claim 13, wherein the second set of training models are derived from one of CT scans and MRI scans.

17. The non-transitory computer readable medium of claim 13, wherein determining the relationship between the subject model and the first set of training models comprises determining a fitting vector.

18. The non-transitory computer readable medium of claim 17, wherein generating the digital 3D model of the object based on the predicted shape is based at least in part on the fitting vector.

19. The non-transitory computer readable medium of claim 13, wherein generating the digital 3D model of the object based on the predicted shape comprises modifying the subject model.

* * * * *